United States Patent [19]

Kubota et al.

[11] Patent Number: 5,210,252

[45] Date of Patent: May 11, 1993

[54] 3-(VINYLPHENYLOXY)PROPYLSILANE COMPOUND

[75] Inventors: Tohru Kubota; Toshinobu Ishihara; Mikio Endo; Katsuhiro Uehara, all of Joetsu, Japan

[73] Assignee: Shin-Etsu Chemical Co., Ltd., Japan

[21] Appl. No.: 933,665

[22] Filed: Aug. 24, 1992

[30] Foreign Application Priority Data

Aug. 26, 1991 [JP] Japan .................. 3-213503

[51] Int. Cl.⁵ .................. C07F 7/08; C07F 7/18
[52] U.S. Cl. .................. 556/445
[58] Field of Search .................. 556/445

[56] References Cited

U.S. PATENT DOCUMENTS

| 4,617,238 | 10/1986 | Givello et al. | 556/445 X |
| 4,645,844 | 2/1987 | Berger et al. | 556/445 X |
| 5,026,810 | 6/1991 | Liu | 556/445 X |
| 5,057,549 | 10/1991 | Herzig et al. | 556/445 X |
| 5,117,028 | 5/1992 | Knorr | 556/445 |
| 5,118,772 | 6/1992 | Herzig et al. | 556/445 X |

Primary Examiner—Paul F. Shaver
Attorney, Agent, or Firm—Parkhurst, Wendel & Rossi

[57] ABSTRACT

The object of the present invention is to provide a styrene type alkoxysilane compound which is useful as a silane coupling agent or a polymerizable monomer and which can easily be synthesized and is not expensive.

A 3-(vinylphenyloxy)propylsilane compound represented by the following general formula:

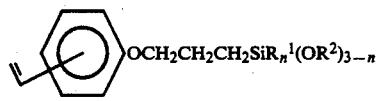

wherein $R^1$ and $R^2$ each represents a hydrocarbon group having 1 to 4 carbon atoms and n is an integer ranging from 0 to 2.

3 Claims, No Drawings

3-(VINYLPHENYLOXY)PROPYLSILANE COMPOUND

BACKGROUND OF THE INVENTION

The present invention relates to a silane compound which is a novel compound having a styrene skeleton highly homopolymerizable and copolymerizable and which is useful as, for instance, a silane coupling agent and a polymerizable monomer material.

Alkoxysilane compounds having functional organic groups have been employed as surface-treating agents for imparting various properties to the surface of a variety of substrates and polymerizable monomers for forming functional polymers through polymerization thereof with other polymerizable monomers.

As styrene type alkoxysilane compounds, there have conventionally been known, for instance, vinylbenzyl trimethoxysilane (Masanori KOKUBO et al., Collected Papers of Polymers, 1981, ,38, p. 201) and vinylphenyl trimethoxysilane (Y. KAWAKAMI et al., Polymer Journal, 1985, 17, p. 1159). However, they require, in the synthesis thereof, the use of unstable and easily polymerizable styrene type Grignard reagents (for instance, vinylbenzyl magnesium halides for the former and vinylphenyl magnesium halides for the latter) and it has been impossible to carry out such reactions in an industrial scale. Moreover, the synthesis of the foregoing compounds requires the use of a large quantity of solvents and a process for removing salts through filtration. Therefore, these compounds are very expensive.

Besides, vinylphenethyl trimethoxysilane has been known as an example of styrene type alkoxysilane compounds and can be prepared by hydrosililating divinylbenzene with hydrogen silane (see U.S. Pat. No. 3,806,549 granted to K. M. Foley). In general, preferred method for preparing alkoxysilanes having functional groups is a hydrosililating method which does not require the use of any solvent and any filtration process, which is economically favorable and which shows good workability and consequently, a variety of coupling agents have presently been synthesized according to this method. In case of the foregoing compound, however, divinylbenzene as a starting material is quite unstable and easily polymerized. Since this material has two vinyl groups having reactivities approximately identical to one another, a compound to which two silane molecules are added is easily produced during the hydrosililation thereof and thus the yield of the intended product is lowered.

SUMMARY OF THE INVENTION

It is accordingly an object of the present invention to provide a styrene type alkoxysilane compound which is useful as a silane coupling agent and a polymerizable monomer and which can easily be prepared in a low cost.

The inventors of this invention have conducted intensive studies of substrates for synthesizing styrene type alkoxysilane compounds to achieve the foregoing object and as a result, have found out that 3-(vinylphenyloxy)-1-propene represented by the following formula[2]:

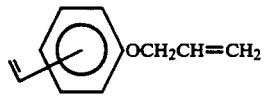

[2]

is most suitable as such a substrate. This 3-(vinylphenyloxy)-1-propene can be hydrosililated to give 3-(vinylphenyloxy)propylsilane compound which is the novel compound according to the present invention and represented by the following general formula[1]:

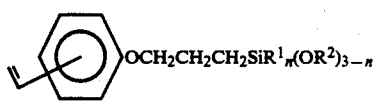

[1]

wherein $R^1$ and $R^2$ each represents a hydrocarbon group having 1 to 4 carbon atoms and n is an integer ranging from 0 to 2.

The substrate, i.e., 3-(vinylphenyloxy)-1-propene of Formula [2] can be prepared according to a known method (for instance, G. F. D'Alelio et al., Journal of Polymer Science, 1967, 5, p. 1245). In this substrate, the double bond of the allyloxy group has an activity in the hydrosililation higher than that of the vinyl group in the styrene skeleton and accordingly, only the intended double bond of the allyloxy group can be subjected to the hydrosililation.

DETAILED EXPLANATION OF THE INVENTION

The novel substance: 3-(vinylphenyloxy)propylsilane compound of the present invention may be prepared according to the following two methods.

The first method comprises hydrosililating 3-(vinylphenyloxy)-1-propene represented by the following formula [2]:

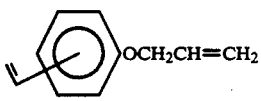

[2]

and a hydrogen silane represented by the following general formula [3]:

$$HSiR^1{}_n(OR^2)_{3-n} \qquad [3]$$

in the presence of a platinum catalyst to give 3-(vinylphenyloxy)-1-propylsilane compound represented by the following general formula [1]:

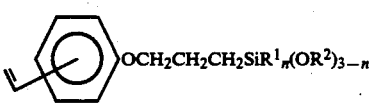

[1]

On the other hand, the second method comprises first hydrosililating 3-(vinylphenyloxy)-1-propene represented by the following formula [2]:

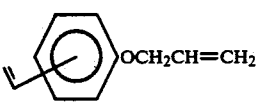

[2]

and a hydrogen silane represented by the following general formula [4]:

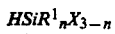
$HSiR^1_nX_{3-n}$ [4]

(wherein X represents a halogen atom) in the presence of a platinum catalyst to give 3-(vinylphenyloxy)propyl halogenosilane compound represented by the following general formula [5]:

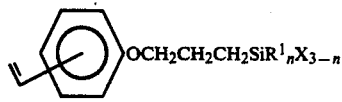
[5]

and then reacting the compound of Formula [5] with an alcohol represented by the following general formula [6]:

$R^2OH$ [6]

to give 3-(vinylphenyloxy)propylsilane compound represented by the following general formula [1]:

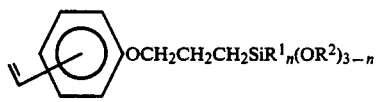
[1]

In the foregoing formulas, the substituents $R^1$ and $R^2$ each is a hydrocarbon group having 1 to 4 carbon atoms such as a methyl, ethyl, propyl, isopropyl or butyl group, X is a halogen atom and n is an integer ranging from 0 to 2.

Examples of the novel compound of Formula [1] according to the present invention, i.e., 3-(vinylphenyloxy)propylsilane compound include 3-(4-vinylphenyloxy)propyl trimethoxysilane 3-(4-vinylphenyloxy)propyl methyl dimethoxysilane, 3-(4-vinylphenyloxy)propyl methyl diethoxysilane 3-(3-vinylphenyloxy)propyl methyl dimethoxysilane and 3-(2-vinylphenyloxy)propyl dimethyl butoxysilane.

Examples of the 3-(vinylphenyloxy)-1-propenes represented by Formula [2] are 3-(2-vinylphenyloxy)-1-propene, 3-(3-vinylphenyloxy)-1-propene and 3-(4-vinylphenyloxy)-1-propene.

Examples of the hydrogen silanes represented by the general formula [3] usable in the present invention include alkoxysilane compounds such as trimethoxysilane, methyl diethoxysilane, ethyl diethoxysilane and dimethyl butoxysilane.

Examples of the hydrogen silanes represented by the general formula [4] usable in the present invention include chlorosilanes such as trichlorosilane, methyl dichlorosilane, ethyl dichlorosilane and dimethyl chlorosilane.

Examples of the alcohols represented by the general formula [6] usable in the present invention include methanol, ethanol, propanol, isopropanol and butanol.

In the synthesis of the compounds according to the present invention, it is preferred to use a reactor equipped with a stirring machine, a thermometer, a reflux condenser and a dropping funnel.

The amount of the platinum catalyst used in the foregoing reactions ranges from 5 to 500 ppm with respect to the amount of 3-(vinylphenyloxy)-1-propene.

The hydrogen silanes represented by the general formulas [3] and [4] each is dropwise added in an amount ranging from to 1.5 eq. with respect to the amount of 3-(vinylphenyloxy)-1-propene. This reaction is desirably carried out at a temperature ranging from 50° to 150° C.

In the reaction of 3-(vinylphenyloxy)propyl halogenosilane compound with the alcohol in the second preparation method, the alcohol is used in an amount of 1.1 to 2 eq. in the absence of any solvent and in the presence of urea as an agent for trapping hydrogen chloride in an amount ranging from 1 to 1.5 eq. A urea.hydrochloride-alcohol phase formed during the reaction can be removed through liquid-liquid separation.

In the preparation of the novel compound according to the present invention, i.e., 3-(vinylphenyloxy)propylsilane compound, 3-(vinylphenyloxy)-1-propene is used as a starting substrate material which can easily be synthesized and is stable. In this 3-(vinylphenyloxy)-1propene, the reactivity of the double bond of the allyloxy group in the hydrosililation is greater than that of the vinyl group of the styrene skeleton and, therefore, only the intended double bond of the allyloxy group can be selectively be hydrosililated to thus easily give 3-(vinylphenyloxy)propylsilane compound according to the present invention without using any solvent and forming salts or the like. The 3-(vinylphenyloxy)propylsilane compound according to the present invention has excellent properties suitable for use as a silane coupling agent for improving properties of composite materials and a polymerizable monomer.

Examples of the present invention will be explained below. However, the present invention is not limited by the examples.

EXAMPLE 1

Preparation of 3-(4-vinylphenyloxy)propyl trimethoxysilane

To a 500 ml glass flask equipped with a stirring machine, a reflux condenser, a thermometer and a dropping funnel, there were added 48.0 g (0.3 mole) of 3-(4-vinylphenyloxy)propene, 0.1 g of a 4% isopropyl alcohol solution of $H_2PtCl_6$ and 0.2 g of BHT. To the mixture, there was dropwise added 36.6 g (0.3 mole) of trimethoxysilane through the dropping funnel at 60° to 70° C. over one hour, followed by ripening at 70° C. for 30 minutes. The reaction solution was distilled to give 66.1 g of a compound having a boiling point of 147°-151° C./3 mmHg. The yield thereof was found to be 78.0%.

The compound was examined by mass spectrometry (MS), nuclear magnetic resonance spectrometry (NMR) and infrared absorption spectrometry (IR) and the following results were obtained.

Results of Measurements

Mass Spectrometric Measurement (MS): m/z (spectral band intensity ratio; assignment): 284 (19, M+), 242 (7), 227 (44), 163 (45), 121 (100, +Si(OCH_3)_3), 91 (32)

Nuclear Magnetic Resonance Spectrometric Measurement (NMR)

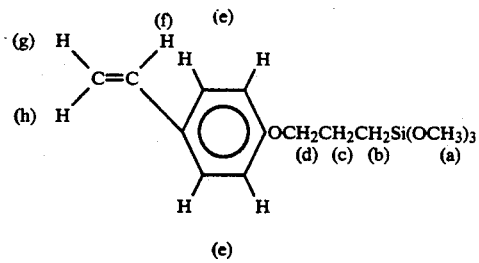

a: 3.44 ppm (s), b: 0.55–0.81 ppm (m), c: 1.58–2.06 ppm (m), d: 3.81 ppm (t), e: 6.56–7.21 ppm (m), f: 6.40 ppm (m), g: 4.85 ppm (m), h: 5.27 ppm (m)

Infrared Absorption Spectrometric Measurement (IR): cm$^{-1}$ 2940, 2840, 1630, 1610, 1515, 1475, 1420, 1305, 1295, 1255, 1200, 1180, 1090, 1020, 1000, 900

These results clearly indicate that the resulting product is a compound represented by the following formula:

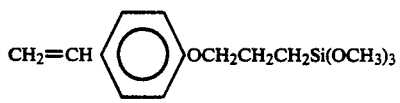

EXAMPLE 2

Preparation of 3-(4-vinylphenyloxy)propyl methyl diethoxysilane

The same procedures used in Example 1 were repeated except that 40.2 g (0.3 mole) of methyl diethoxysilane was substituted for 36.6 g (0.3 mole) of trimethoxysilane to give 70.8 g of a product having a boiling point of 132°–136° C./1 mmHg. The yield thereof was found to be 80.1%.

The compound was examined by mass spectrometry (MS), nuclear magnetic resonance spectrometry (NMR) and infrared absorption spectrometry (IR) and the following results were obtained.

Results of Measurements

Mass Spectrometric Measurement (MS): m/z (spectral band intensity ratio; assignment): 294 (22, M$^+$), 252 (70), 237 (7), 207 (10), 175 (41), 133 (100, $^+SiCH_3(OCH_2CH_3)_2$), 105 (22), 77 (47)

Nuclear Magnetic Resonance Spectrometric Measurement (NMR)

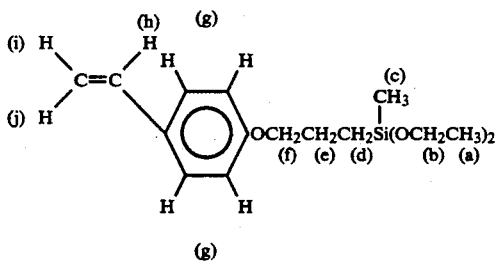

a: 1.17 ppm (t), b: 3.72 ppm (q), c: 0.08 ppm (s), d: 0.51–0.79 ppm (m), e: 1.57–2.05 ppm (m), f: 3.60 ppm (t), g: 6.55–7.20 ppm (m), h: 6.40 ppm (m), i: 4.88 ppm (m), j: 5.28 ppm (m)

Infrared Absorption Spectrometric Measurement (IR): cm$^{-1}$ 2970, 2940, 2870, 1630, 1610, 1580, 1520, 1475, 1445, 1420, 1395, 1300, 1250, 1180, 1115, 1110, 1020, 995, 955, 900

These results clearly indicate that the resulting product is a compound represented by the following formula:

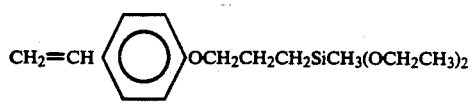

EXAMPLE 3

Preparation of 3-(4-vinylphenyloxy)propyl methyl diethoxysilane

To a 500 ml glass flask equipped with a stirring machine, a reflux condenser, a thermometer and a dropping funnel, there were added 48.0 g (0.3 mole) of 3-(4-vinylphenyloxy)-1-propene, 0.1 g of a 4% isopropyl alcohol solution of H$_2$PtCl$_6$ and 0.2 g of BHT. To the mixture, there was dropwise added 34.5 g (0.3 mole) of methyl dichlorosilane through the dropping funnel at 60° to 70° C. over one hour, followed by ripening at 70° C. for 30 minutes. To the reaction solution, there were dropwise added 39.6 g (0.66 mole) of urea and then 28.8 g (0.9 mole) of methanol at room temperature, the lower phase, i.e., urea.hydrochloride-methanol phase was removed through liquid-liquid separation and the upper phase was distilled to give 65.2 g of a compound having a boiling point of 140°–145° C./2 mmHg. The compound was examined by mass spectrometry (MS), nuclear magnetic resonance spectrometry (NMR) and infrared absorption spectrometry (IR) and it was confirmed that the results of these measurements were the same as those observed for the compound obtained in Example 2. The yield thereof was found to be 73.8%.

The novel compound of the present invention, i.e., 3-(vinylphenyloxy)propylsilane compound thus synthesized has excellent properties suitable for use as a silane coupling agent for improving properties of composite materials and a polymerizable monomer. If the compound is used as a silane coupling agent, it is favorable as a treating agent or additive for, for instance, inorganic materials such as glass fibers, clay, silica, quartz powder, mica and alumina; and organic materials such as polyethylene, polypropylene, polystyrene, unsaturated polyesters, natural rubbers and synthetic rubbers. The compound can thus widely be used and show its effect as a primer for the improvement of adhesion of sealing agents, the improvement in the mechanical properties and adhesiveness, the stabilization of electric properties, the improvement in properties of resins or the improvement in the surface properties of composite materials. On the other hand, if it is used as a polymerizable monomer, polymers having hydrolyzable alkoxysilyl groups on the side chains can be obtained by radical-copolymerizing the compound and other various radical-polymerizable monomers such as styrenes, acrylates, methacrylates, vinyl esters, ethylene, propylene, vinyl chloride, butadiene, isoprene, chloroprene and α-olefins in the presence of polymerization initiators such as organic peroxides or azo compounds. These polymers have excellent adhesiveness to a variety of substrate since they have good crosslinking abilities under mild conditions in the presence of moisture and have alkoxy groups which have excellent affinity to inorganic materials and metallic materials. It would be anticipated that these polymers can be applied to high functional plastics and functional film materials since the application thereof can ensure the improvement of various physical properties of these substrates, such as heat resistance, weatherability, low-temperature resistance, gas permeability and impact resistance.

What is claimed is:

1. A 3-(vinylphenyloxy)propylsilane compound represented by the following general formula [1]:

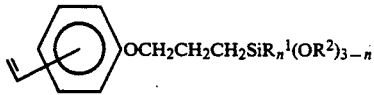

wherein $R^1$ and $R^2$ each represents a hydrocarbon group having 1 to 4 carbon atoms and n is an integer ranging from 0 to 2.

2. The 3-(vinylphenyloxy)propylsilane compound as set forth in claim 1 wherein R, is a methyl or ethyl group and n is 0.

3. The 3-(vinylphenyloxy)propylsilane compound as set forth in claim 1 wherein $R^1$ is a methyl group, $R^2$ is a methyl or ethyl group and n is 1.